(12) United States Patent
Lyu

(10) Patent No.: US 9,528,093 B2
(45) Date of Patent: Dec. 27, 2016

(54) **RECOMBINANT POLYNUCLEOTIDE AND A TRANSGENIC *FLAMMULINA VELUTIPES* CARRYING THE SAME**

(71) Applicant: MYCOMAGIC BIOTECHNOLOGY CO., LTD., New Taipei (TW)

(72) Inventor: Ying-Tzu Lyu, New Taipei (TW)

(73) Assignee: MYCOMAGIC BIOTECHNOLOGY CO., LTD., New Taipei (TW)

( * ) Notice: Subject to any disclaimer, the term of this patent is extended or adjusted under 35 U.S.C. 154(b) by 23 days.

(21) Appl. No.: 14/464,779

(22) Filed: Aug. 21, 2014

(65) Prior Publication Data
US 2016/0051664 A1 Feb. 25, 2016

(51) Int. Cl.
| | | |
|---|---|---|
| *C12N 15/80* | (2006.01) | |
| *C12N 15/33* | (2006.01) | |
| *C12N 7/00* | (2006.01) | |
| *A61K 39/12* | (2006.01) | |
| *A61K 39/00* | (2006.01) | |

(52) U.S. Cl.
CPC ............ *C12N 7/00* (2013.01); *A61K 39/0002* (2013.01); *A61K 39/12* (2013.01); *C12N 15/80* (2013.01); *A61K 2039/60* (2013.01); *C12N 2730/10034* (2013.01); *C12N 2730/10134* (2013.01); *C12N 2730/10151* (2013.01); *C12N 2800/22* (2013.01)

(58) Field of Classification Search
None
See application file for complete search history.

(56) References Cited

U.S. PATENT DOCUMENTS

2014/0123345 A1   5/2014   Lyu

FOREIGN PATENT DOCUMENTS

TW    201416443 A    5/2014

OTHER PUBLICATIONS

Thomas Pniewski, International Journal of Molecular Sciences, 2013, 14:1978-1998.*
Chayama et al., Journal of Gastroenterology and Hepatology, 2011, 26:13-18.*
Van Herck et al. (1998) "Long-term persistence of anti-HBs after vaccination with a recombinant DNA yeast-derived hepatitis B vaccine: 8-year results," Vaccine. 16(20): 1933-1935.
World Health Organization Health Topics Vaccines, downloaded Mar. 12, 2016 from http://who.int/topics/vaccines/en.
Lin (Jun. 12, 2014) "Establishment of homologous selectable system and development of hepatitis B virus oral vaccine in Flammulina velutipes," Master's dissertation Department of Biochemical Science and Technology, National Taiwan University. pp. II-III, 4-7, 16-18, 27-29, 67-68, 77-78, 80-81, 83-84.—relevant portion is English Abstract.
Guo (Sep. 4, 2008) "Development and Application of Mushroom Heterologous Gene Expression Systems," Doctoral thesis, Graduate Institute of Microbiology and Biochemistry, National Taiwan University.—relevant portion is English translation of the Abstract and English translation of Figure descriptions for Figs. 3-2 and 3-3.

* cited by examiner

*Primary Examiner* — Stacy B Chen
(74) *Attorney, Agent, or Firm* — Lathrop & Gage LLP; James H. Velema, Esq.

(57) ABSTRACT

The invention provides a recombinant polynucleotide comprising a truncated glyceraldehyde-3-phosphate dehydrogenase (gpd) promoter and a modified HBV S protein gene and a transgenic *Flammulina velutipes* carrying the recombinant polynucleotide. The invention surprisingly found that after administering the transgenic *Flammulina velutipes* to a subject, the subject can successfully generate an antibody against HBV. Therefore, the transgenic *Flammulina velutipes* can be used as a vaccine against HBV.

16 Claims, 6 Drawing Sheets

Fig. 1

SEQUENCE LISTING

```
<160> NUMBER OF SEQ ID NOS: 2

<210> SEQ ID NO 1
<211> LENGTH: 1205
<212> TYPE: DNA
<213> ORGANISM: Artificial Sequence
<220> FEATURE:
<223> OTHER INFORMATION: gpd promoter sequence

<400> SEQUENCE: 1
gcattacttc gctctacgat gaggttttgc acagaacctt aggtcgggtg tcgggcccct      60
gctgacccga gctacttaat actttctttc cttcgacttt gctcaaactt aaacgagagt     120
aagtaccggt tctgacagtc actcaatatt cgtctgatgc tctctcgggg gaaatctctc     180
tccaacgacc attctttatt atctgaagct ggttgtcttc gatcgagtat acgacgtcct     240
ggggcttgtc ttagtctcac gaaggccgac tctatcgctc taggactcgc ttgatataga     300
tgtgcgtaac tttaagtgag ctcgtattca tcttattcca ttcccattga gtcgtgggtc     360
cagcattttg ttcgagagag tcaagactcg aggataccgc tagtcgcctg tggtctggat     420
cgttccttct atgttcggtg tctggagcat ggcctttcta gactcttggc tggtactgga     480
cgaccaatca cgaggtgcct gtggcgcaca ttatggctct ccgtgtgctc cagccaatta     540
ggttccgggg aggggttatg cattagaaac gatctgttca tctgaaaggt ggtatcgcgt     600
ttgttgtgtg gatgaccacc ctagatgagg cctggatgat actgccttaa aattggaggc     660
gcgtccaggg cgcgtcgttc tccgagtctg ttccgctgat gaattttgcc tgctcgacat     720
cgtttctgcg gacatgcgat cgacgagatc tttgcgttag acgccgttgg gaagggactc     780
ggaggtgggt ttagacctgc gtggtagaag aatgggacga gtatatgagt agagtaccgc     840
gtcgataccg cgtaaccgtg catgtgctac tactccttga ccgctgattg gttgcgaact     900
```

-continued

```
cgacatgatc taggtcgtcc tcgtctggac tcctaatcaa gagagacaag agaatggttg      960
aggagctgct caaattttgg cggataacgt cgtcggtatc ctatgaatct acgttgtgta     1020
tctctaatgc tttgtacgtc tttgacgcgg taagaattta ggacggaatg cagacgaaat     1080
gacagcgatg acgtaacatc cgattatcag cgcgacagta taaaaggcgc agaattttga     1140
catctctcct ttctgcaacc gccatcttcc tcacttcaat ctctttacca tctcctcatc     1200
tacaa                                                                 1205

<210> SEQ ID NO 2
<211> LENGTH: 699
<212> TYPE: DNA
<213> ORGANISM: Artificial Sequence
<220> FEATURE:
<223> OTHER INFORMATION: Modified HBV S protein gene

<400> SEQUENCE: 2
atggagaaca tcacatccgg atttctcgga ccgctgctcg tgcttcaagc tgggttcttc       60
ttgttgacga gaatcctcac gatcccgcaa tccctcgact cgtggtggac ttctctcaac      120
tttctcggtg gcacgaccgt ttgcctgggc cagaattcgc aaagtccaac ctccaatcac      180
tcgccaacct cttgtcctcc gacttgtcct gggtatcgct ggatgtgcct cgccgtttc      240 atcatctttc tcttcattct gctgctctgc ctcatcttct tgttggtgct gctggactat      300
caaggcatgt tgcccgtctg tcctctcatt cctggatcct ccacgacctc tacgggaccc     360
tgccgcacct gcatgacgac ggcgcaaggc acctccatgt atccctcctg ctgctgtacc      420
aaaccttcgg atgggaactg cacctgcatt cccatcccat cctcctgggc tttcgggaaa     480
ttcctctggg aatgggcctc cgcccgtttc tcctggctct ctctcctcgt gccatttgtt     540
caatggtttg tcggactgtc tcccactgtt tggctgtccg tgatctggat gatgtggtac     600
tggggaccaa gtctgtacag catcttgagt ccctttctcc cgctgctccc gatcttcttc    660
tgcctttggg tctacattgc tagtcatgat gaactgtaa                           699
```

RECOMBINANT POLYNUCLEOTIDE AND A TRANSGENIC *FLAMMULINA VELUTIPES* CARRYING THE SAME

The instant application contains a Sequence Listing, which has been submitted electronically in ASCII format, and is hereby incorporated by reference in its entirety. The ASCII copy, created on Aug. 19, 2014, is named US2806_sequence_listing_ST25.text and is 3 kb in size.

FIELD OF THE INVENTION

The invention relates to a recombinant polynucleotide and a transgenic *Flammulina velutipes* carrying the recombinant polynucleotide. Particularly, the recombinant polynucleotide of the invention comprises a truncated glyceraldehyde-3-phosphate dehydrogenase (gpd) promoter and a modified Hepatitis B Virus (HBV) S protein gene, also known as small HBV surface protein (SHBs) or HBV surface antigen (HBsAg), and the transgenic *F. velutipes* carrying the same can be used as a vaccine against HBV infection.

BACKGROUND OF THE INVENTION

HBV infects the liver and causes an inflammation commonly referred to as viral hepatitis. The disease is endemic in certain populations, such as China and other parts of Asia. About a third of the world's population, more than 2.4 billion people have been infected with the HBV. HBV infection may either be acute, otherwise known as self-limiting, or chronic, otherwise known as long-standing. Acute infection with HBV is associated with acute viral hepatitis, an illness that begins with general ill-health, loss of appetite, nausea, vomiting, body aches, mild fever, dark urine, and then progresses to development of jaundice. The illness lasts for a few weeks and then gradually improves in most affected people. A few patients may have more severe liver disease (fulminant hepatic failure), and may die as a result of it. The infection may be entirely asymptomatic and may go unrecognized. Chronic infection with HBV may be either asymptomatic or may be associated with a chronic inflammation of the liver, chronic hepatitis, leading to liver cirrhosis over a period of several years. This type of infection dramatically increases the incidence of hepatocellular carcinoma. Chronic carriers are encouraged to avoid consuming alcohol as it increases their risk for liver cirrhosis and cancer. Approved medications for treatment of HBV include lamivudine, adefovir, tenofovir, telbivudine and entecavir. However, drug resistance is a main problem of the drug treatment in view of mutations of the HBV genes.

The HBV belongs to the Hepadnaviridae, a group of hepatotropic DNA viruses. HBV is a blood-borne virus, comprising a small, partially double-stranded DNA genome, carrying four extensively overlapping open reading frames, consisting of an inner nucleocapsid, comprising the HBV core protein ("HBcAg"), viral polymerase and viral DNA, surrounded by a membranous envelope containing HBV surface antigens ("HBsAg"). The viral envelope contains three different, but related surface antigen proteins, large (L), medium (M) and small (S), which share a common carboxy terminal region but have different amino termini, arising from variable use of initiation triplets at different points within a continuous open reading frame.

US 20060159705 provides a method for the production of a HBV antigen suitable for use in a vaccine, the method comprising purification of the antigen in the presence of cysteine, to vaccines comprising such antigens. US 20070280962 provides HBV core antigen particles that are characterized by multiple immunogen specificities. US 20110165194 relates to an HBV vaccine comprising an entire hepatitis B virus surface antigen of L protein, M protein and S protein, in which the produced antigens form virus-like particles, and a multi-antigen vaccine further comprising an HBV core antigen in addition to the entire surface antigen, and a method for preparing the same. Although a number of HBV vaccines have been disclosed, most of these vaccines are administered by injection, which need skilled medicians and higher cost. Oral vaccines are more convenient in administration and thus can be widely applies to reduce HBV infection.

Molecular pharming has attracted extensive attention in production of various pharmaceutical proteins, including enzymes, vaccines, antibodies, hormones, etc. Liz Richter et al., Nat Biotechnol. 2000 November; 18(11):1167-71. use tobacco leaves and potato tuber to produce oral HBV vaccine. Edible mushrooms are regarded as appropriate hosts for production of recombinant proteins, especially for the development of edible vaccines. Arakawa et al. use potato leaves and tubers, tobacco leaves, tomato, lettuce and rice to produce cholera vaccine. However, transgenic plants are planted in an open environment, so using transgenic plants for protein production may cause impacts on health and the environment. The use of mushrooms for molecular pharming has all the advantages of plant-based systems coupled with unique benefits including complete duplication, fast growth, scale-up production under controlled conditions and less gene contamination. US 20140123345 provides a truncated glyceraldehyde-3-phosphate dehydrogenase promoter and a construct comprising the promoter of the invention operably linked to a heterologous transcribable polynucleotide molecule and a mushroom comprising the construct. However, this prior art patent application only provides expressible truncated glyceraldehyde-3-phosphate dehydrogenase promoter in mushroom and it still needs extensive research works and overcome technical problems to achieve the purpose of using mushroom as molecular pharming.

SUMMARY OF THE INVENTION

The invention provides a recombinant polynucleotide, comprising a glyceraldehyde-3-phosphate dehydrogenase (gpd) promoter having the nucleotide sequence selected from SEQ ID NO: 1 and a modified HBV S protein gene having the nucleotide sequence as shown in SEQ ID NO: 2. In one embodiment, the recombinant polynucleotide of the invention can be expressed in a mushroom. In certain embodiments, the mushroom is *Flammulina, Agaricus, Pleurotus* or *Lentinula*; more preferably, *F. velutipes, Pleurotus ostreatus, Pleurotus pulmonarius*, or *Pleurotus populinus*; most preferably, *F. velutipes*.

The invention also provides a vector comprising the recombinant polynucleotide of the invention. In one embodiment, the vector comprises a mushroom plasmid; preferably, the plasmid is pCAMBIA-0390. In one embodiment, the vector is pCAMBIA-0390-MM-Fv-B-001.

The invention also provides a transgenic *F. velutipes*, which is deposited with Deutsche Sammlung von Mikroorganismen and Zellkulturen under deposit number DSM 27789. The transgenic *F. velutipes* of the invention comprises a truncated gpd promoter having a nucleotide sequence as shown in SEQ ID NO: 1 and a modified HBV S protein gene having the nucleotide sequence as shown in SEQ ID NO: 2.

The invention further provides a vaccine composition, comprising the transgenic *F. velutipes* of the invention. In one embodiment, the vaccine composition can be used as a medicament or a food. In one embodiment, the vaccine composition of the invention can be used as a medicament or a food. In one embodiment, the vaccine composition comprises mycelia or fruiting bodies of the transgenic *F. velutipes* of the invention. In one embodiment, the vaccine composition is administered intranasally, by spraying, intravenously, intradermally, subcutaneously, orally, by aerosol or intramuscularly. In another embodiment, the dose of the transgenic *F. velutipes* ranges from 2.0 g to 10 g dry weight the transgenic *F. velutipes* per kg body weight. In a further embodiment, the vaccine composition further comprises an adjuvant or an immune enhancer or stimulant.

BRIEF DESCRIPTION OF THE DRAWING

FIG. 1 shows the synthesized procedure of mHBsAg.

DETAILED DESCRIPTION OF THE INVENTION

Figure 2:
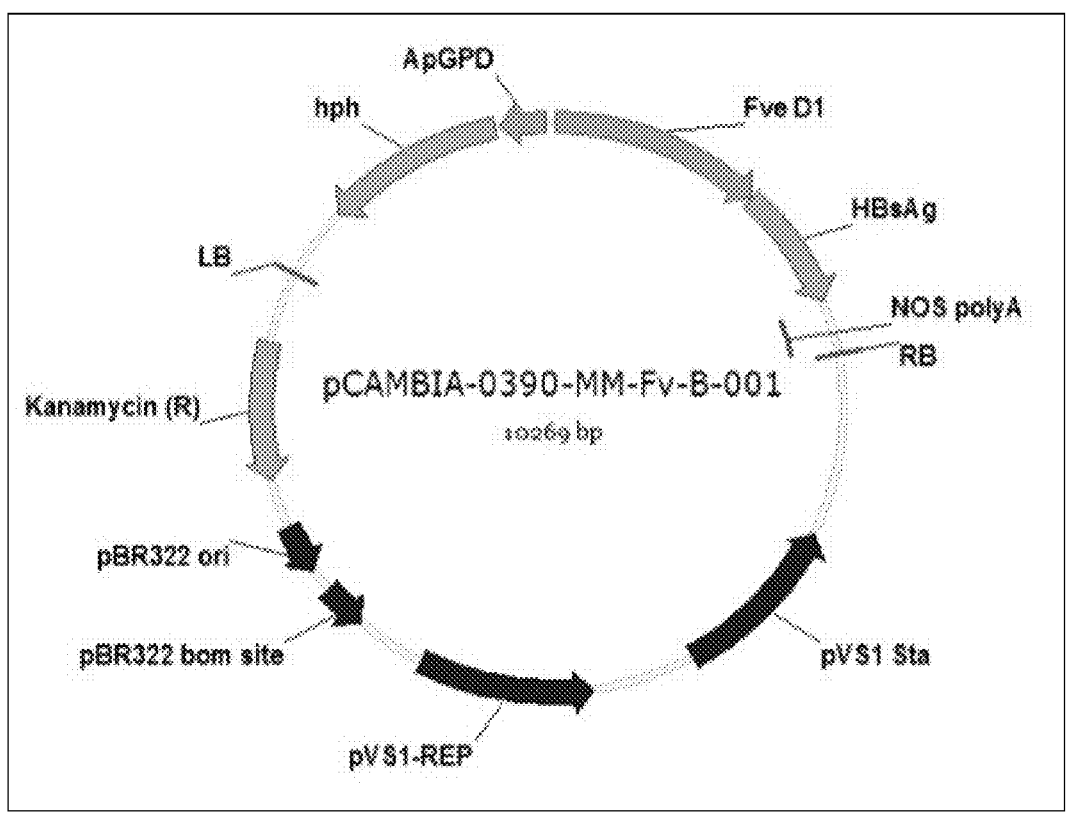
FIG. 2 shows the map of vector pCAMBIA-0390-MM-Fv-B-001.

The invention creates a recombinant polynucleotide comprising a truncated glyceraldehyde-3-phosphate dehydrogenase (gpd) promoter and a modified HBV S protein gene and a transgenic *F. velutipes* carrying the recombinant polynucleotide. The invention surprisingly found that after administering the transgenic *F. velutipes* to a subject, the subject can successfully generate an antibody against HBV. Therefore, the transgenic *F. velutipes* can be used as a vaccine against HBV.

The following description is of an embodiment by way of example only and without limitation to the combination of features necessary for carrying the invention into effect. The headings provided are not meant to be limiting of the various embodiments of the invention. Terms such as "comprises," "comprising," "comprise," "includes," "including," and "include" are not meant to be limiting. In addition, the use of the singular (a/an) includes the plural, and "or" means "and/or" unless otherwise stated. Unless otherwise defined herein, all technical and scientific terms used herein have the same meaning as commonly understood by one of ordinary skill in the art.

As used herein, the terms "HBV" and "hepatitis B virus" are used interchangeably and refer to any member of the hepadnaviridae (see e.g. Ganem and Schneider in Hepadnaviridae (2001) "The viruses and their replication" (pp 2923-2969), Knipe D M et al., eds. Fields Virology, 4th ed. Philadelphia, Lippincott Williams & Wilkins or subsequent edition). Extensive phylogenetic analyses have led to the classification of hepatitis B viruses into 8 major genotypes (A to H), which show sequence divergence by at least 8%. The various HBV genotypes show distinct geographic distribution and can display heterogeneous disease symptoms and/or clinical outcome. The various HBV were classified in nine different subtypes (ayw1, ayw2, ayw3, ayw4, ayr, adw2, adw4, adrq+ and adqr−) in connection with HBsAg-associated serology (see review by Mamum-Al Mahtab et al., 2008, Hepatobiliary Pancrease Dis Int 5:457; Schaeffer, 2007, World Gastroenterol. 7:14; Norder et al., 1993, J. Gen Virol. 74:1341). Each genotype and serotype encompasses different HBV strains and isolates. An isolate corresponds to a specific virus isolated from a particular source of HBV (e.g. a patient sample or other biological HBV reservoir) whereas a strain encompasses various isolates which are very close each other in terms of genomic sequences.

As used herein, the term "vector" refers to both expression and non-expression vectors and includes viral as well as non viral vectors, including extrachromosomal vectors (e.g. multicopy plasmids) and integrating vectors designed for being incorporated into the host chromosome(s). Particularly important in the context of the invention are vectors for transferring nucleic acid molecule(s) in a viral genome (so-called transfer vectors), vectors for use in immunotherapy (i.e. which are capable of delivering the nucleic acid molecules to a host organism) as well as expression vectors for use in various expression systems or in a host organism.

As used herein, the term "operatively linked" refers to two nucleic acid sequences that are related physically or functionally. For example, a promoter or regulatory DNA sequence is said to be "associated with" a DNA sequence that codes for a RNA or a protein if the two sequences are operatively linked or so situated that the regulator DNA sequence will affect the expression level of the coding or structural DNA sequence.

As used herein, the phrase "polynucleotide construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecules have been linked in a functionally operative manner. The terms "polynucleotide construct" and "construct" are used interchangeably herein.

As used herein, the term "transformed" refers to a cell, tissue, organ, or organism into which a foreign polynucleotide molecule, such as a construct, has been introduced. Preferably, the polynucleotide molecule introduced is integrated into the genomic DNA of the recipient cell, tissue, organ, or organism so that the introduced polynucleotide molecule is inherited by subsequent progeny.

As used herein, the term "expression" includes any step involved in the production of the polypeptide including, but not limited to, transcription, post-transcriptional modification, translation, post-translational modification, and secretion.

In one aspect, the invention provides a recombinant polynucleotide, comprising a glyceraldehyde-3-phosphate dehydrogenase (gpd) promoter having the nucleotide sequence selected from SEQ ID NOs: 1 and a modified HBV S protein gene having the nucleotide sequence as shown in SEQ ID NO: 2.

The sequence of SEQ ID NO: 1 and their production refer to US 20140123345, which is incorporated herein in its entirety. The sequences of SEQ ID NOs: 1 and 2 are listed as follows:

```
                                                                SEQ ID NO: 1
   1    GCATTACTTC GCTCTACGAT GAGGTTTTGC ACAGAACCTT AGGTCGGGTG TCGGGCCCCT

61    GCTGACCCGA GCTACTTAAT ACTTTCTTTC CTTCGACTTT GCTCAAACTT AAACGAGAGT

121    AAGTACCGGT TCTGACAGTC ACTCAATATT CGTCTGATGC TCTCTCGGGG GAAATCTCTC

181    TCCAACGACC ATTCTTTATT ATCTGAAGCT GGTTGTCTTC GATCGAGTAT ACGACGTCCT

241    GGGGCTTGTC TTAGTCTCAC GAAGGCCGAC TCTATCGCTC TAGGACTCGC TTGATATAGA

301    TGTGCGTAAC TTTAAGTGAG CTCGTATTCA TCTTATTCCA TTCCCATTGA GTCGTGGGTC

361    CAGCATTTTG TTCGAGAGAG TCAAGACTCG AGGATACCGC TAGTCGCCTG TGGTCTGGAT

421    CGTTCCTTCT ATGTTCGGTG TCTGGAGCAT GGCCTTTCTA GACTCTTGGC TGGTACTGGA

481    CGACCAATCA CGAGGTGCCT GTGGCGCACA TTATGGCTCT CCGTGTGCTC CAGCCAATTA

541    GGTTCCGGGG AGGGGTTATG CATTAGAAAC GATCTGTTCA TCTGAAAGGT GGTATCGCGT

601    TTGTTGTGTG GATGACCACC CTAGATGAGG CCTGGATGAT ACTGCCTTAA AATTGGAGGC

661    GCGTCCAGGG CGCGTCGTTC TCCGAGTCTG TTCCGCTGAT GAATTTTGCC TGCTCGACAT

721    CGTTTCTGCG GACATGCGAT CGACGAGATC TTTGCGTTAG ACGCCGTTGG GAAGGGACTC

781    GGAGGTGGGT TTAGACCTGC GTGGTAGAAG AATGGGACGA GTATATGAGT AGAGTACCGC

841    GTCGATACCG CGTAACCGTG CATGTGCTAC TACTCCTTGA CCGCTGATTG GTTGCGAACT

901    CGACATGATC TAGGTCGTCC TCGTCTGGAC TCCTAATCAA GAGAGACAAG AGAATGGTTG

961    AGGAGCTGCT CAAATTTTGG CGGATAACGT CGTCGGTATC CTATGAATCT ACGTTGTGTA

1021    TCTCTAATGC TTTGTACGTC TTTGACGCGG TAAGAATTTA GGACGGAATG CAGACGAAAT

1081    GACAGCGATG ACGTAACATC CGATTATCAG CGCGACAGTA TAAAAGGCGC AGAATTTTGA

1141    CATCTCTCCT TTCTGCAACC GCCATCTTCC TCACTTCAAT CTCTTTACCA TCTCCTCATC

1201    TACAA

SEQ ID NO: 2
   1    ATGGAGAACA TCACATCCGG ATTTCTCGGA CCGCTGCTCG TGCTTCAAGC TGGGTTCTTC

61    TTGTTGACGA GAATCCTCAC GATCCCGCAA TCCCTCGACT CGTGGTGGAC TTCTCTCAAC

121    TTTCTCGGTG GCACGACCGT TTGCCTGGGC CAGAATTCGC AAAGTCCAAC CTCCAATCAC

181    TCGCCAACCT CTTGTCCTCC GACTTGTCCT GGGTATCGCT GGATGTGCCT GCGCCGTTTC

241    ATCATCTTTC TCTTCATTCT GCTGCTCTGC CTCATCTTCT TGTTGGTGCT GCTGGACTAT

301    CAAGGCATGT TGCCCGTCTG TCCTCTCATT CCTGGATCCT CCACGACCTC TACGGGACCC

361    TGCCGCACCT GCATGACGAC GGCGCAAGGC ACCTCCATGT ATCCCTCCTG CTGCTGTACC

421    AAACCTTCGG ATGGGAACTG CACCTGCATT CCCATCCCAT CCTCCTGGGC TTTCGGGAAA

481    TTCCTCTGGG AATGGGCCTC CGCCCGTTTC TCCTGGCTCT CTCTCCTCGT GCCATTTGTT

541    CAATGGTTTG TCGGACTGTC TCCCACTGTT TGGCTGTCCG TGATCTGGAT GATGTGGTAC

601    TGGGGACCAA GTCGTACAG CATCTTGAGT CCCTTTCTCC CGCTGCTCCC GATCTTCTTC

661    TGCCTTTGGG TCTACATTGC TAGTCATGAT GAACTGTAA
```

The mHbsAg used in the invention is modified from the HBV S protein gene so that it can be expressed in a mushroom. The HBV S protein can be used as an antigen to induce immune response. The authentic HBV surface antigen can be recovered from plasma of chronic HBV carrier as particles of about 22 nm composed of two proteins known as P24 and its glycosylated derivative GP27, both of which are encoded by the 226 amino acid coding sequence on the HBV genome known as the S protein coding sequence, or HBV S-gene. The invention modifies the HBV S protein gene and surprisingly found that the modified sequence as shown in SEQ ID NO:2 is optimum to be expressed in mushrooms; preferably, *Flammulina, Agaricus, Pleurotus* and *Lentinula*; more preferably, *F. velutipes, Pleurotus ostreatus, Pleurotus pulmonarius*, and *Pleurotus populinus*; most preferably, *Flammulina velutipes*.

In the invention, the gpd promoter is operatively linked to mHbsAg; preferably, to a 3' transcription termination of polynucleotide molecule. The recombinant polynucleotide can include additional regulatory polynucleotide molecules, which includes but is not limited to the 5' untranslated regions (5' UTR) of an mRNA polynucleotide molecule which can play an important role in translation initiation and can also be a genetic component in a mushroom expression construct. These additional upstream and downstream regulatory polynucleotide molecules may be derived from a source that is native or heterologous with respect to the other elements present on the promoter construct.

In one aspect, the invention provides a vector comprising the recombinant polynucleotide of the invention. A great variety of expression systems can be used to as vectors of the invention. Such vectors include, among others, chromosomal, episomal and virus-derived vectors, e.g., vectors derived from various mushroom plasmids, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system vectors may contain control regions that regulate as well as engender expression. Generally, any system or vector suitable to maintain, propagate or express polynucleotides and/or to express the recombinant polynucleotides in a host may be used for expression in this regard. The appropriate DNA sequence may be inserted into the expression system by any of a variety of well-known and routine techniques, such as, for example, those set forth in Sambrook et al., Molecular Cloning, A Laboratory Manual. Preferably, the vector contains pCAMBIA-0390; more preferably, the vector is pCAMBIA-0390-MM-Fv-B-001.

In one aspect, the invention provides a transgenic *F. velutipes*, which is deposited with Deutsche Sammlung von Mikroorganismen und Zellkulturen under deposit number DSM 27789. The deposit containing a transgenic *F. velutipes* has been deposited with the Deutsche Sammlung von Mikroorganismen und Zellkulturen Gmbh (herein ("DSMZ"), Inhoffenstraße 7B 38124 Braunschweig Germany on Sep. 25, 2013 and assigned deposit number 27789.

The deposited strain contains the modified small HBV surface protein gene (mHbsAg) having the nucleotide sequence as shown in SEQ ID NO: 2 and gpd promoter (SEQ ID NO: 1). The sequence of the polynucleotides contained in the deposited strain, as well as the amino acid sequence of the polypeptide encoded thereby, are controlling in the event of any conflict with any description of sequences herein.

*F. velutipes* cells can be transformed using the expression vectors of the invention, whereby the host cells are transformed with one or more of the recombinant polynucleotides of the invention, as described above. A transformation construct containing a promoter of the present invention may be introduced into *F. velutipes* cells by any transformation method. Methods and materials for transforming mushrooms by introducing a mushroom expression construct into a mushroom genome in the practice of this invention can include any of the well-known and demonstrated methods including electroporation, *Agrobacterium*-mediated transformation and protoplast transformation. The resulting transformed *F. velutipes* cells are cultured for several generations and then selected to obtain a HBV antigen expressible *F. velutipes*, which was then deposited according to the Budapest Treaty on Sep. 25, 2013 with DSMZ-Deutsche Sammlung von Mikroorganismen and Zellkulturen GmbH (DSMZ), Mascheroder Weg 1b, D-38124 Braunschweig, Germany, and assigned deposit number DSM 27789.

In another aspect, the invention provides a vaccine composition, comprising the transgenic *F. velutipes* of the invention. In one embodiment, the vaccine composition of the invention can be used as a medicament or a food. In one embodiment, the vaccine composition comprises mycelia or fruiting bodies of the transgenic *F. velutipes* of the invention.

The transgenic *F. velutipes* of the invention is generally formulated into pharmaceutically acceptable vaccine compositions. The vaccine compositions are formulated according to the route of administration and are compatible with the active antigenic agent. The active antigenic agent is, for example, one or more transgenic *F. velutipes* according to the invention.

The useful dosage of the vaccine composition of the invention to be administered will vary depending on the age, weight and animal vaccinated, the mode and route of administration and the type of pathogen against which vaccination is sought. The vaccine may comprise any dose of the transgenic *F. velutipes*, sufficient to evoke an immune response. Doses ranging between 2.0 g to 200 g dry weight the transgenic *F. velutipes* per kg body weight are suitable doses. Doses between 3.0 g to 150 g, 3.0 g to 100 g, 3.0 g to 50 g, 3.0 g to 30 g, 3.0 g to 25 g, 300 g to 20 g, 3.0 g to 15 g, 3.0 g to 10 g or 3.0 g to 6.0 g the transgenic *F. velutipes* per kg body weight are more preferred; more preferably, 3.0 g to 5.5 g, 3.0 g to 4.3 g or 4.3 g to 5.6 g the transgenic *F. velutipes* per kg body weight.

Optionally, one or more compounds having adjuvant activity may be added to the vaccine. Adjuvants are non-specific stimulators of the immune system. They enhance the immune response of the host to the vaccine. Examples of adjuvants known in the art are Freund's Complete and Incomplete adjuvant, vitamin E, non-ionic block polymers, MDP (muramyl dipeptides), ISCOMs (immune stimulating complexes), Saponins, mineral oil, vegetable oil, and Carbopol. Optionally, the vaccine composition includes immune enhancers or stimulants (co-administered or administered in series, e.g., before or after vaccination). Suitable immune stimulants include, but are not limited to, cytokines, growth factors, chemokines, supernatants from cell cultures of lymphocytes, monocytes, cells from lymphoid organs, cell preparations or cell extracts (e.g. *Staphylococcus aureus* or lipopolysaccharide preparations) or mitogens.

In one embodiment, the vaccine composition may comprise a pharmaceutically acceptable carrier. A pharmaceutically acceptable carrier may be as simple as water. Another suitable carrier is e.g. a solution of physiological salt concentration. Other examples of pharmaceutically acceptable carriers or diluents useful in the present invention include stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

For administration to animals or humans, the vaccine according to the present invention can be given inter alia intranasally, by spraying, intravenously, intradermally, subcutaneously, orally, by aerosol or intramuscularly. Preferred methods for reason of convenience are administration by spraying, intranasal administration and oral administration.

EXAMPLES

Example 1

Preparation of Vector Carrying Recombinant Polynucleotide of the Invention

Figure 1:
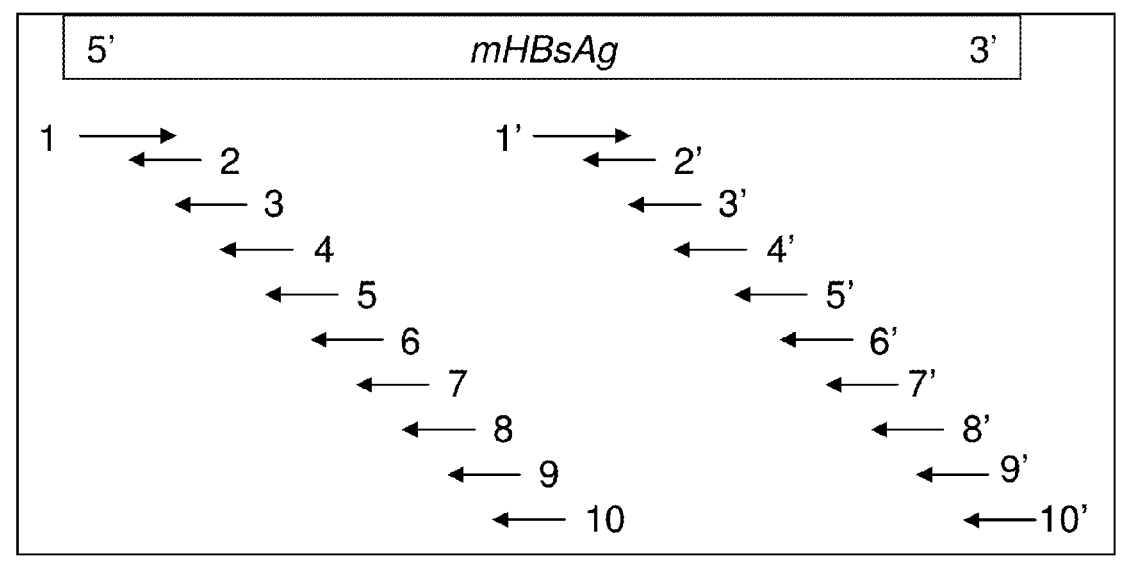

The mHbsAg sequence as shown in SEQ ID NO:2 is synthesized by PCR. The procedure of synthesis of mHbsAg sequence is showed in FIG. 1. Twenty primers, 1 to 10 and 1' to 10', were designed, according to the codon usage bias of *F. velutipse*, to synthesize the fragments of SEQ ID NO:2 continuously and subsequently. SEQ ID NO:2 was synthesized by combining these fragments with overlap PCR.

The truncated glyceraldehyde-3-phosphate dehydrogenase promoter having SEQ ID NO: 1 is called as Fve D1 in the examples. The plasmid pCAMBIA-0390 (CAMBIA, Canberra, Australia) with a size of 6.8 kb is a binary vector used in *Agrobactrium*-mediated transformation system. LBA4404 582 bp T-DNA harboring nopaline synthase (NOS) 3' UTR poly A signal and pUC9's multiple cloning site (MCS) was constructed into the plasmid between 25 bp LB (left border) and 25 bp RB (Right border). The backbone of the vector contains aminoglycoside phosphotransferase which is kanamycin resistance gene used as bacterial selectable marker.

The vector, pCAMBIA-039-MM-Fv-B001 (FIG. 2) was constructed by inserting Fve D1 containing first intron, mHBsAg and hygromycin B resistance gene (hygromycin B phosphotransferase, hph) as *Agrobacterium tumefaciens* selectable marker into the MCS of pCAMBIA-0390. Sequence of the construct is confirmed by sequencing (Genomics, Taipei).

*Escherichia coli* DH5α (GIBCOBRL, Life Technologies, Grand Island, N.Y., USA), which was used as the host cell for DNA manipulation and plasmids conservation, was cultured in Luria-Bertani (LB; Sigma Chem. Co., St. Louis, Mo., USA) broth medium or agar plate at 37° C. with shaking at 250 rpm.

The *Escherichia coli* DH5α harboring pCAMBIA-039-MM-Fv-B001 was cultured in LB containing 50 μg/ml kanamycin at 37° C. with shaking at 250 rpm for 16 hours. After centrifuging and removing supernatant, the plasmids were extracted by Plasmid miniprep purification kit (Genemark, Taipei).

A single colony of *Agrobacterium tumefaciens* on LB agar plate was picked and inoculated into 3 ml of LB broth medium at 30° C. with shaking at 250 rpm. After 48 hours, 1 ml of the *A. tumefaciens* solution was added to 100 ml LB and then cultured overnight at the same condition as mentioned above. When *A. tumefaciens* grew to $OD_{600}$ value as 1.5-2.0, the bacteria solution was centrifuged at 3000 g at 4° C. for 10 minutes. Then the supernatant was removed and the cell sediments was resuspended in 100 ml of 4° C. sterilized water. The procedures of centrifugation and resuspensionwere repeated 6 times. Lastly, the cells were resuspended in 400 μl of 4° C. sterilized 10% glycerol and divided into 40 μl per microcentrifuge tube and stored at −80° C. as *A. tumefaciens* competent cells.

2 μl of plasmids were added to 40 μl of *A. tumefaciens* competent cells and the resulting mixture was kept on ice for 2 min, followed by transferring to 0.2 cm gap cuvette (BTX, San Diego, Calif., USA). The plasmids subsequently transformed into *A. tumefaciens* by electroporation (Capacitor: 25 μF, Resistor: 200 ohms, Voltage: 1.25 kV/cm, Electric field strength: 12.5 kV/cm, Pulse time: 5.0 msec) via BTX Electro Cell manipulator 630. After the electroporation, 400 μl of LB was added into the bacteria solution and placed into microcentrifuge tube. After 2.5 hours, 50 μl of solution was plated on LB agar plate with 50 μg/ml kanamycin and then cultured at 30° C. for 48 hours. The putative *A. tumefaciens* transformants were screened via colony PCR analysis with specific primers.

*F. velutipes* mycelia were grown and maintained on CYM agar or broth containing 0.2% tryptone, 0.2% yeast extract, 1% maltose, and 2% glucose at 25° C. for 2-3 weeks and then the cultured mycelia agar plate were punched with a puncher as modified mycelial pellets (MMPs). The *A. tumefaciens* strains harboring the target plasmids were cultivated 24 hours in LB medium containing 50 μg/ml kanamycin at 28° C. with shaking at 250 rpm, followed by mixing with *F. velutipes* MMPs in induction medium (IM) that contained 200 M acetosyringone for 6 h at 23° C. After incubation, the MMPs were subsequently transferred to fresh IM agar plate at 23° C. for 3-6 days. Then, the treated MMPs were washed with sterile water five times to remove *Agrobacterium* and transferred to selectable agar plates containing 30 μg/ml hygromycin B and 200 mM cefotaxime (MDBio, Taipei, Taiwan) at 25° C. for 2-3 weeks until hygromycin B-resistant mycelia of *F. velutipes* appeared. (IM; see Table 1 below).

TABLE 1

| Formulation of induction medium (IM) | |
| --- | --- |
| Constituent | g/L |
| $K_2HPO_4$ | 2.05 |
| $KH_2PO_4$ | 1.45 |
| NaCl | 0.15 |
| $MgSO_4 \cdot 7H_2O$ | 0.5 |
| $CaCl_2 \cdot 2H_2O$ | 0.067 |
| $FeSO_4 \cdot 7H_2O$ | 0.0025 |
| $(NH4)_2SO_4$ | 0.5 |
| MES (pH 5.3) | 8.53 |
| Glucose* | 1.8 |
| Glycerol | 5 |
| Acetosyringone | 200 μM |

Note:
IM agar plate contain 0.9 g/L glucose

Figure 3:
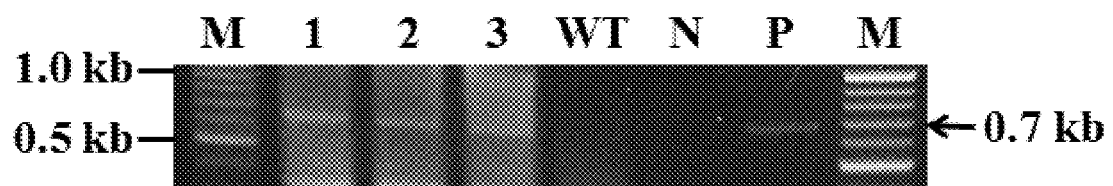
FIG. 3 shows the mHBsAg gene detection of transgenic *F. velutipes* by PCR. Lane P: positive control using plasmid pCAMBIA-0390-MM-Fv-B-001; lane M: DNA marker; lane WT: *F. velutipes* wild type.

The hygromycin B-resistant mycelia of *F. velutipes* putative transformants, which were subcultured several times to obtain the stable ones, were subsequently screened via PCR analysis, which were used to confirm the gene integration of mHBsAg into genomes. The genomic DNA of transformants was extracted by Genomic DNA mini kit (Geneaid, Taipei). The PCR products was subjected to gel electrophoresis to comfirm the appearance of specific mHBsAg fragments 0.7 kb. The data is showed in FIG. 3. The selected transgenic *F. velutipes* was deposited at DSMZ with deposit number 27789.

Example 2

In vivo Production of anti-HBV Antibody by Administration with the Transgenic *F. velutipes* of the Invention The transgenic *F. velutipes* mycelia obtained from Example 1 were seeded at sawdust bottles at 25° C. for 1-2 months. After the mycelia grew, the bottles were placed at 15° C. for 2-4 weeks to induce the growth of fruiting bodies. The fruiting bodies were harvested and dried to obtain powder. 50 mg sample powder was mixed with 0.5 ml protein extraction buffer (50 mM sodium phosphate, 300 mM NaCl, 1 mM PMSF, 0.1% Triton X-100, pH=7.4) on ice for 1 hour. After centrifuging at 13,000 g for 30 min, the supernatant was collected as the tota soluble protein (TSP). Protein concentrations were determined using Pierce™ BCA Protein Assay kit (Pierce Biotechnology, USA). The bovine serum albumin (Pierce, Rockford, USA) was used to prepare standards (0 mg/ml, 0.2 mg/ml, 0.4 mg/ml, 0.6 mg/ml, 0.8 mg/ml and 1 mg/ml). The 10 μl of standards and the samples were added 200 μl BCA reagent (Reagent A:B, 50:1, v/v) on 96-well microplate at dark for 30 minutes. The absorbance values at 562 nm were measured using a 96-well plate reader (VERSAmax, Sunnyvale, Calif.).

Figure 4:
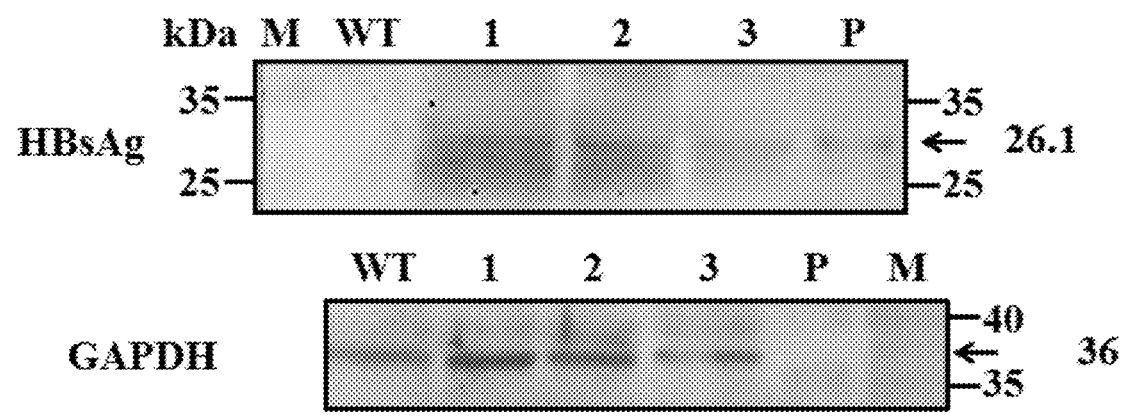
FIG. 4 shows the HBsAg protein detection of transgenic *F. velutipes* by western blot assay. Lane P: positive control using commercial HBsAg protein purchased from Abcam; lane M: protein marker; lane WT: *F. velutipes* wild type.

The mHBsAg protein in the TSP was measured by western blot analysis. The fruiting bodies and mycelia of *F. velutipes* transformants and wild type were collected and subsequently ground in liquid nitrogen with a mortar and pestle. A total of 50 mg sample powder were mixed with 0.5 ml protein extraction buffer on ice for 1 hours. After centrifuging the mixture at 13000 g for 30 min, the supernatant was collected as TSP, boiled with sample buffer [50 mM Tris-HCl (pH 7.4), 2% SDS, 0.1% Bromophenol blue, 10% Glycerol, 400 mM DTT and 800 mM 2-mercaptoethanol] for 20 mins, separated by 12% sodium dodecyl sulfate polyacrylamide gel electrophoresis (SDS-PAGE). The protein samples were transferred via Trans-Blot Electrophoretic Transfer Cell (Bio-Rad, USA) to a PVDF membrane (Millipore, Bedford, Mass., USA). Protein detection was performed using a mouse monoclonal anti-HBsAg antibody (Abcam, Taiwan, Taipei) and a goat anti-mouse IgG antibody conjugated alkaline phosphatase (AP), with the NBT/BCIP reaction (PerkinElmer) as described by the manufacturers. The data is showed in FIG. 4.

The quantification of mHBsAg protein in the TSP of mycelia and fruiting bodies was measured by using the SURASE B-96 (GENERAL BIOLOGICALS CORP., Taiwan, Taipei). Plate wells coated with Anti-HBsAg antibody were incubated with the 50 μl TSP and anti-HBsAg antibody conjugated peroxidase for 90 mins at 37° C. Each sample assay was repeated in triplicate for each plate. At the end of this incubation period, plate wells were washed six times with washing soultion, 100 μl of TMB-HRP microwell substrate (BioFX, Owings Mills, Md.) was added to each well. After 30 mins at 37° C., the reaction was stopped by the addition 100 μl of 2 N sulfuric acid and the absorbance at 450 nm in each well was measured using a 96-well plate reader (VERSAmax, Sunnyvale, Calif.).

Figure 5:
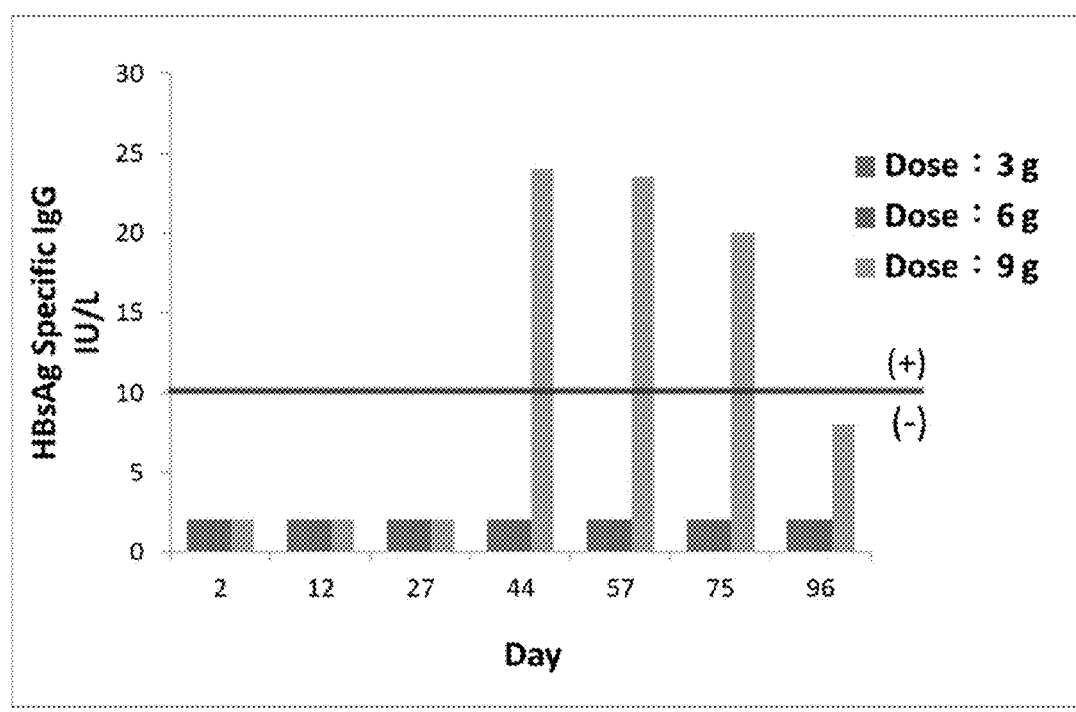
FIG. 5 shows the titer of HBs antibody produced in the pigs administered with the transgenic *F. velutipes* mycelia.

9 g of the transgenic *F. velutipes* mycelia powder were orally administered to pigs once three days for 6 weeks. Subsequently, the pigs were administered once a week for two weeks. At the second day after completing the administration, blood samples of the pigs were taken to measure antibody titer by using the Elecsys Anti-HBs (Roche). Subsequently, blood samples were taken after each 10 days for ELISA assay. As shown in FIG. 5, at 44 day, 57 day and 75 day after administration, the blood samples contain anti-HBV antibody, so it shows that the transgenic *F. velutipes* mycelia of Example 1 indeed can induce immune response in the pigs.

Figure 6:
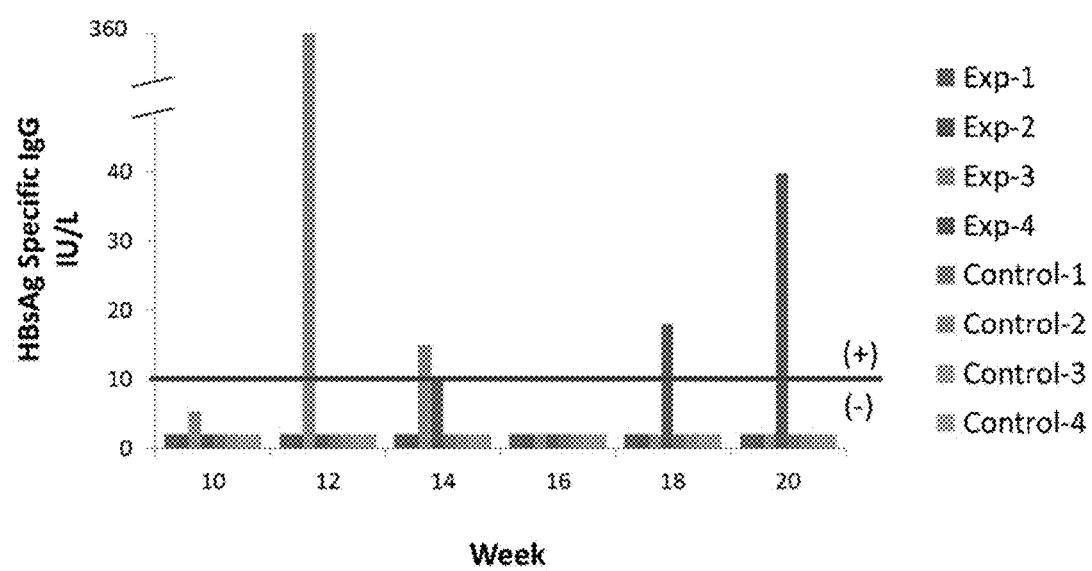
FIG. 6 shows the titer of HBs antibody produced in the pigs administered with the transgenic *F. velutipes* fruiting bodies.

9 g of the transgenic *F. velutipes* fruiting bodies powder were orally administered to four pigs once three days for 6 weeks. After that, the pigs were administered once a week for 14 weeks. The blood samples were taken after 6-week administration to measure antibody titer with ELISA assay. After that, the blood samples were taken once two weeks for 8 times. As shown in FIG. 6, two pigs appear antibody response after 12 and 18 weeks, respectively. It shows that the recombinant *Flammulina velutipes* fruiting bodies of Example 1 indeed can induce immune response in the pigs.

What is claimed is:

1. A recombinant polynucleotide, comprising a glyceraldehyde-3-phosphate dehydrogenase (gpd) promoter comprising the nucleotide sequence set forth in SEQ ID NO: 1 and a modified HBV S protein gene comprising the nucleotide sequence set forth in SEQ ID NO: 2.

2. A transgenic mushroom comprising the recombinant polynucleotide of claim 1, wherein the mushroom is selected from the group consisting of Flammulina, Agaricus, Pleurotus and Lentinula.

3. The transgenic mushroom of claim 2, wherein the mushroom is selected from the group consisting of Flammulina velutipes, Pleurotus ostreatus, Pleurotus pulmonarius, and Pleurotus populinus.

4. A vector comprising the recombinant polynucleotide of claim 1.

5. The vector of claim 4, which comprises a mushroom plasmid.

6. The vector of claim 5, wherein the plasmid is pCAMBIA-0390.

7. The vector of claim 5, which is pCAMBIA-0390-MM-Fv-B-001.

8. A transgenic F. velutipes, which is deposited with Deutsche Sammlung von Mikroorganismen and Zellkulturen (DSMZ) under deposit number DSM 27789.

9. The transgenic F. velutipes of claim 8, comprising a truncated gpd promoter comprising the nucleotide sequence set forth in SEQ ID NO: 1 and a modified HBV S protein gene comprising the nucleotide sequence set forth in SEQ ID NO: 2.

10. An immunogenic composition, comprising the transgenic F. velutipes of claim 9.

11. The immunogenic composition of claim 10, wherein the composition is comprised in a medicament or a food.

12. The immunogenic composition of claim 11, wherein the composition comprises a dose of the transgenic Flammulina velutipes ranging from 2.0 g to 200 g dry weight of transgenic F. velutipes per kg body weight.

13. The immunogenic composition of claim 10, wherein the composition is formulated for administering to a subject by a route of administration selected from the group consisting of intranasally, by spraying, intravenously, intradermally, subcutaneously, orally, by aerosol, and intramuscularly.

14. The immunogenic composition of claim 10, which further comprises an adjuvant or an immune enhancer or stimulant.

15. The immunogenic composition of claim 10, which is in an oral form.

16. The immunogenic composition of claim 10, comprising mycelia or fruiting bodies of the transgenic *F. velutipes* of claim 9.

\* \* \* \* \*